ID#

United States Patent
Brown

(12) United States Patent
(10) Patent No.: US 9,066,952 B1
(45) Date of Patent: Jun. 30, 2015

(54) REJUVENATING HAIR OIL SYSTEM AND METHOD OF USE

(76) Inventor: Carolyn Brown, Monroe, NY (US)

( * ) Notice: Subject to any disclaimer, the term of this patent is extended or adjusted under 35 U.S.C. 154(b) by 1091 days.

(21) Appl. No.: 13/101,453

(22) Filed: May 5, 2011

Related U.S. Application Data

(60) Provisional application No. 61/343,980, filed on May 6, 2010.

(51) Int. Cl.
*A61K 35/56* (2006.01)
*A61K 36/53* (2006.01)
*A61K 36/87* (2006.01)

(52) U.S. Cl.
CPC ...................................... *A61K 36/53* (2013.01)

(58) Field of Classification Search
None
See application file for complete search history.

(56) References Cited

U.S. PATENT DOCUMENTS

| | | | |
|---|---|---|---|
| 5,108,749 A | | 4/1992 | Hua |
| 5,407,675 A | * | 4/1995 | Etemad-Moghadam ..... 424/401 |
| 6,103,272 A | | 8/2000 | Keeney |
| 6,194,468 B1 | | 2/2001 | Hattori et al. |
| 7,025,955 B2 | | 4/2006 | Siddiqui et al. |
| 7,166,300 B1 | | 1/2007 | Dascalu |
| 2004/0142853 A1 | | 7/2004 | Patt |
| 2005/0003024 A1 | | 1/2005 | Oblong et al. |
| 2006/0057075 A1 | * | 3/2006 | Arkin et al. ...................... 424/47 |
| 2008/0145331 A1 | | 6/2008 | Bruning et al. |
| 2008/0248138 A1 | * | 10/2008 | Greco ........................... 424/725 |
| 2008/0267899 A1 | | 10/2008 | Leskaj |
| 2009/0117146 A1 | | 5/2009 | Khan et al. |
| 2010/0322887 A1 | * | 12/2010 | Aoki et al. ................... 424/70.1 |
| 2011/0212157 A1 | * | 9/2011 | Edelson et al. ............... 424/443 |

FOREIGN PATENT DOCUMENTS

KR  20090005479 A  * 1/2009

* cited by examiner

*Primary Examiner* — Chris R Tate
(74) *Attorney, Agent, or Firm* — Goldstein Law Offices, P.C.

(57) ABSTRACT

A rejuvenating hair oil system with a pre-shampoo treatment and a post-shampoo treatment and a method of use that promotes healthful hair growth and improved hair appearance. The pre-shampoo treatment is a mixture of oils that provides moisturization as well as healing the scalp. The post-shampoo treatment is a mixture that contains a variety of oils and extracts derived from fruit, herbs, plants, animals as well as the flowers and seeds of various trees. The natural oil carriers are generally also act as moisturizers. Other oils and extracts provide antioxidants, anti-inflammatory compounds, antimicrobials, and penetrating compounds. The pre-shampoo treatment is applied to the hair and scalp five to ten minutes before shampooing and the hair is covered with a plastic cap. In between shampooing, a small amount of the post-shampoo treatment is applied to the hair and scalp as needed.

3 Claims, 1 Drawing Sheet

REJUVENATING HAIR OIL SYSTEM AND METHOD OF USE

CROSS-REFERENCE TO RELATED APPLICATIONS

This application is a nonprovisional utility application of the provisional patent application, Ser. No. 61/343,980 filed in the United States Patent Office on May 6, 2010 and claims the priority thereof.

BACKGROUND OF THE INVENTION

The invention relates generally to a rejuvenating hair oil system and a method of using the rejuvenating hair oil system. More particularly, the invention relates to a rejuvenating hair oil system with a pre-shampoo treatment and a post-shampoo treatment and a method of using the rejuvenating hair oil system that promotes healthful hair growth and improved hair appearance.

Hair thinning is a common problem for both men and women, and can occur as a result of aging, over-treatment with dyes, perms and straighteners or as a common side effect of chemotherapy. Dry or brittle hair breaks off close to the scalp or excessive amounts of hair fall out from the follicle, creating hair loss. People with this type of hair loss want to prevent additional loss by keeping the remaining hair supple and soft and as well as encourage new growth from the follicles in the scalp. Many products for the hair have ingredients that can contribute to hair loss, especially if the hair is fragile or previously damaged. Ninety percent of shampoos contain surfactants such as sodium lauryl sulfate, a harsh surfactant that is irritating to the scalp and strips the hair, making it weaker and more prone to becoming damaged.

Hair thinning and loss is often a cause of great psychological stress to the person symbolizing a loss of youth, health and vitality. Many people try to coax the hair into regrowing by various treatments applied topically to the scalp or by ingesting certain drugs. Most experience unsatisfactory results. For example, the FDA has approved two drugs for the treatment of male pattern baldness, but only a lower strength of one of the drugs is approved for use by women with alopecia or baldness. Neither drugs address the quality of the hair that may grow back. Other vitamins, minerals and botanical extracts have been proposed for oral ingestion to improve the quality and quantity of the patient's hair.

Many cosmetic products have been tried over the centuries from bird droppings in ancient times to today's various amino acids, vitamins, minerals, colloidal silver, copper chelates and botanical extracts such as saw palmetto, and tree nut oils, all claiming to promote hair regrowth, to improve the appearance of the hair, making it thicker and more luxurious. Most are applied to the hair, and the scalp, and one has been proposed for application into the scalp.

While these units may be suitable for the particular purpose employed, or for general use, they would not be as suitable for the purposes of the present invention as disclosed hereafter. While these units may be suitable for the particular purpose employed, or for general use, they would not be as suitable for the purposes of the present invention as disclosed hereafter.

SUMMARY OF THE INVENTION

It is an object of the invention to produce a rejuvenating hair oil system that provides a treatment that moisturizes the hair and scalp before shampooing. Accordingly, the rejuvenating hair oil system provides a pre-shampoo treatment containing natural oils that are mixtures of long chain fatty acids that moisturize the scalp and hair.

It is another object of the invention to produce a rejuvenating hair oil system the prevents damage from surfactants such as sodium lauryl sulfate that are in most shampoos. Accordingly, the rejuvenating hair oil system provides a pre-shampoo oil treatment that acts as a barrier when placed on the hair before washing and protects the hair from these harsh ingredients during the shampooing process, resulting in stronger hair.

It is still another object of the invention to produce a rejuvenating hair oil system that provides a treatment that promotes healing of the scalp before shampooing. Accordingly, the rejuvenating hair oil system provides a pre-shampoo treatment containing natural oils that are mixtures of medium chain fatty acids and medium chain fatty acid derivatives that promote scalp healing, curb itching and prevent dry scalp. The pre-shampoo treatment contains essential fragrance oils that provide a pleasing scent as well as other beneficial properties.

It is a further object of the invention to produce a rejuvenating hair oil system that provides a treatment that promotes a healthy scalp in between shampooing. Accordingly, the rejuvenating hair oil system provides a post-shampoo treatment containing oils and extracts with antioxidants, anti-inflammatory compounds, antimicrobials, and penetrating compounds to promote scalp health. The post-shampoo treatment contains essential fragrance oils that provide a pleasing scent as well as other beneficial properties.

It is yet another object of the invention to produce a rejuvenating hair oil system that provides a treatment that promotes healthful hair growth in between shampooing. Accordingly, the rejuvenating hair oil system provides a post-shampoo treatment containing natural oils that are mixtures of long chain fatty acids that moisturize the scalp and hair.

It is yet a further object of the invention to produce a rejuvenating hair oil system that provides a method of use that moisturizes the hair and scalp before shampooing and provides a treatment for the hair and scalp in between shampooing. According, the method of use provides a pre-shampoo treatment that is applied to the hair and scalp ten to twenty minutes before shampooing and covered with a plastic cap and provides a post-shampooing treatment that is applied to the hair and scalp as needed in between shampooing.

The invention is a rejuvenating hair oil system with a pre-shampoo treatment and a post-shampoo treatment and a method of use that promotes healthful hair growth and improved hair appearance. The pre-shampoo treatment is a mixture of oils that provides moisturization as well as healing the scalp. The post-shampoo treatment is a mixture that contains a variety of natural oils and extracts derived from fruit, herbs, plants, animals as well as the flowers and seeds of various trees. The natural oil carriers generally also act as moisturizers. Other oils and extracts provide antioxidants, anti-inflammatory compounds, antimicrobials, and penetrating compounds. The pre-shampoo treatment is applied to the hair and scalp five to ten minutes before shampooing and the hair is covered with a plastic cap. In between shampooings, a small amount of the post-shampoo treatment is applied to the hair and scalp as needed.

To the accomplishment of the above and related objects the invention may be embodied in the form illustrated in the accompanying tables. Attention is called to the fact, however, that the tables are exemplary only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
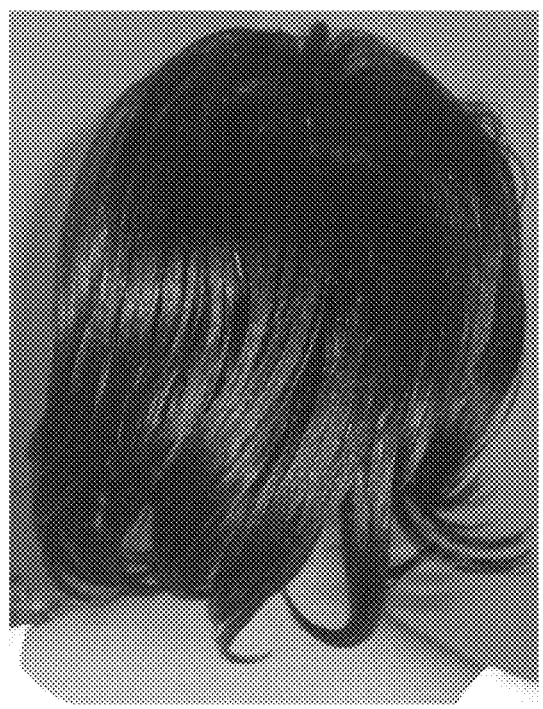
FIG. 1 is a photograph of a user taken at the beginning of treatment with the invention

The present invention provides a system of hair restoring oil treatments that includes a pre-shampoo treatment and a post-shampoo treatment that promote healthful hair growth and improved hair appearance. The system is provided to treat a scalp and hair of a user, especially if the user has dry or brittle hair, by softening and restoring suppleness. The invention provides treatments that are healthful and beneficial to the scalp and softens and restores suppleness to the hair. The pre-shampoo treatment is applied about five to ten minutes before shampooing, but can be left on for up to one hour, even overnight, depending on the condition of the hair, for example, if the hair is extremely dry, stressed, chemically treated and damaged. The pre-shampoo oil treatment acts as a barrier when placed on the hair prior to washing and protects the hair from harsh surfactants during the shampooing process. The hair is wrapped and covered with a plastic cap, covering the hair until shampooing. After shampooing, the hair is dried, and the post-shampoo treatment is applied to the scalp and massaged into the scalp and allowed to remain. The hair has a plurality of roots near the scalp. The post-shampoo treatment is applied to the roots of the hair. The post-shampoo treatment is selectively applied a plurality of times between shampooing as desired by the user.

The pre-shampoo treatment composition is an essentially non-aqueous blend of oils. The blend contains oils derived from fruit and seeds of various trees, and when combined in the pre-shampoo treatment, produce a synergistic effect on the hair and scalp. The oils in the pre-shampoo treatment provide moisturization, along with other benefits, such as healing the scalp as well as preventing dry scalp. The pre-shampoo treatment is composed of oils such as organic extra virgin olive oil, organic grape seed oil, jojoba oil, organic black castor oil, organic coconut oil, and organic sesame oil and an essential oil, such as organic lavender oil, used as a fragrance. Olive oil, grape seed oil and jojoba oil are mixtures of long chain fatty acids. The olive oil and grape seed oil are both carriers for the other ingredients as well as moisturizers for the scalp and hair. The other oils are medium length fatty acids and medium length fatty acids derivatives which have anti-itching and healing attributes. Lavender oil may be present with or without one or more of the essential oils selected from the group consisting of orange oil and ylang ylang oil. Lavender oil is the preferred essential oil because of its additional qualities of providing a calming and relaxing effect.

Olive oil, known also by its INCI (International Nomenclature of Cosmetic Ingredients) name, *olea europaea* fruit oil, is mechanically extracted from olives, which are the fruit of the olive tree. Olive oil is a mixture of fatty acids, primarily oleic acid, along with palmitic acid and linoleic acid and small amount of other fatty acids. Along with grape seed oil, it is the carrier for the other oils in the pre-shampoo treatment composition. Olive oil also adds gloss and shine to the hair as well as moisturizes the hair and scalp.

Grape seed oil, know also by its INCI name, *vitis vinifera* seed oil, is mechanically pressed from the seeds of grapes. Grape seed oil is a mixture of fatty acids, primarily linoleic acid with significant amounts of oleic, palmitic, and stearic acids. Grape seed oil also contains 0.8 to 1.5% compounds such as phenols and steroids that can act as antioxidants to protect the hair and scalp from harsh chemicals found in other hair care products. It is primarily a carrier but also has beneficial moisturizing attributes.

Jojoba oil is a liquid wax produced in the seed of the jojoba plant (*Simmondsia chinensis*) plant. Jojoba oil, also known by its INCI name, *simmondsia chinensis* seed oil, is a mixture of extremely long (C36-C46) straight-chain wax esters, making jojoba more similar to human sebum than other plant oils. Jojoba oil is used as a moisturizer and a carrier. Jojoba oil is mainly eiconsenoic and docosenoic acid with a small amount of oleic acid.

Coconut oil, also know by its INCI name, *cocos nucifera* oil, is extracted from the kernel or meat of matured coconut harvested from the coconut palm (*Cocos nucifera*). Coconut oil is composed predominately of glyceryl esters of medium chain fatty acids (MCFA) mainly lauric and myristic acid. Coconut oil is a safe and effective skin moisturizer.

Black castor oil, also known by its INCI name, *ricinus communis* seed oil, is an all purpose healing oil, commonly used for hair and scalp problems. The oil seals moisture in the hair with a protective coat. It is the only oil in nature that is a fatty acid triglyceride of ricinoleic acid which is thought to be responsible for its healing abilities. Ricinoleic acid is an effective topical treatment for pruritus (itching) of the scalp.

Sesame oil, also known as *sesamum indicum* oil is derived from sesame seeds which come from a flowering plant in the genus *Sesamum*. Sesame oil, when topically applied, relieves dryness. It is mainly linoleic and oleic fatty acids.

Example 1

The composition of an embodiment of the pre-shampoo treatment is disclosed in Table 1.

TABLE 1

| Ingredient | Minimum | Maximum |
| --- | --- | --- |
| Olive oil | 25% | 45% |
| Grape seed oil | 25% | 45% |
| Black castor oil | 5% | 25% |
| Coconut oil | 5% | 25% |
| Sesame oil | 0 | 1% |
| Fragrance | 0 | 1% |

The olive oil and grape seed oil may vary from the minimum of 25% to a maximum of 45%. The black castor oil and coconut oil may vary from the minimum of 5% to a maximum of 25%, but are in a ratio of about 2 parts black castor oil to three parts coconut oil to each other.

Example 2

The composition of a further embodiment of the pre-shampoo treatment is disclosed in Table 2.

TABLE 2

| Ingredient | Minimum | Maximum | Preferred |
| --- | --- | --- | --- |
| Olive oil | 25% | 45% | 42% |
| Grape seed oil | 25% | 45% | 45% |

TABLE 2-continued

| Ingredient | Minimum | Maximum | Preferred |
|---|---|---|---|
| Jojoba oil | 1% | 25% | 3% |
| Black castor oil | 1% | 25% | 2% |
| Coconut oil | 1% | 25% | 3% |
| Sesame oil | 0 | 1% | 1% |
| Lavender oil | 0 | 5% | 3% |

The olive oil and grape seed oil and may vary from the minimum of 25% to a maximum of 45%, but approximately are about in a 1:1 ratio to each other. The jojoba oil, black castor oil and coconut oil may vary from the minimum of 1% to a maximum of 25%. The jojoba oil and coconut oil are in a ratio of about 1:1 to each other and the black castor oil and coconut oil are in a ratio of about 2 parts black castor oil to three parts coconut oil to each other.

Example 3

The composition of another embodiment of the pre-shampoo treatment is disclosed in Table 3. The carrier is olive oil in combination with coconut oil, with the ratio of olive oil to coconut oil is generally about a 5:3 ratio.

TABLE 3

| | Minimum | Maximum |
|---|---|---|
| Olive oil | 50% | 70% |
| Coconut oil | 25% | 50% |
| Black castor oil | 2% | 10% |
| Sesame oil | 1% | 5% |
| Fragrance | 0 | 2% |

It is understood that the above are examples of the composition of the pre-shampoo treatment and that other oils in the carrier and other essential fragrance oils may be used while adhering to the inventive concept. It is also understood that the ratios of the ingredients disclosed hereinabove may be adjusted within the presented ranges. Such variations are contemplated as being a part of the present invention.

The post-shampoo treatment is predominantly a non-aqueous mixture of oils that also includes a small amount of an aqueous component. The product does not have emulsifiers and must be shaken vigorously before application to mix the aqueous component into the oil component. The mixture contains a variety of oils and extracts derived from fruit, herbs, plants, animals as well as the flowers and seeds of various trees. These oils are generally long chain fatty acids that blend well together but each contains other components that are derived from their own natural sources that give each a unique characteristics suitable for a revitalizing hair oil system. The carrier systems disclosed hereinbelow are both carriers for the other oils as well as moisturizers. Other oils provide antioxidants, anti-inflammatory compounds, antimicrobials, and penetrating compounds to promote scalp and hair health. The post-shampoo treatment contains essential fragrance oils that provide a pleasing scent as well as other beneficial properties. The post-shampoo treatment is composed of oils and extracts such as for example, but not limited to, amla extract, argan oil, avocado oil, extract of Brahmi, organic coconut oil, emu oil, organic grape seed oil, organic jojoba oil, organic nettle extract, organic rosemary extract, organic sage extract, sweet almond oil, tea tree oil, vitamin E, VATIKA® Enriched Coconut Hair Oil (VATIKA® is the registered trademark of Dabur India Limited, New Delhi, India) and an essential fragrance oil. The essential oil is selected from the group consisting of organic lavender oil, orange oil, and ylang ylang oil and the product selectively contains at least one essential oil in the post-shampoo treatment. Lavender oil is the preferred essential oil because of its additional qualities of providing a calming and relaxing effect. The post-shampoo treatment may optionally also contain lemongrass oil.

Amla extract, also known by its INCI name, *emblica officinalis* extract, is prepared from the dried fruit of the Indian gooseberry tree (*Phyllanthus emblica*, syn. *Emblica officinalis*) which have been soaked in oil for several days to extract the oil soluble vitamins from the fruit. Amla extract is a non-aqueous extract that is used as an aid for improving the health of hair and scalp, and brings forth a rich, natural shine and soft texture, but also helps rejuvenate hair that is dull and damaged. The extraction oil is preferably sesame oil, but other oils such as coconut oil are possible.

Argan oil, also know by its INCI name, *argania spinosa* kernel oil, is an oil produced from the kernels of the argan tree. It primarily has oleic, alpha-linolenic, and palmitic fatty acids. Argan oil is exceptionally rich in natural vitamins such as vitamin E and carotenes, as well as rich in phenols and phenolic acid.

Avocado oil, also known under its INCI name, *persea gratissima* oil, is pressed from the fleshy pulp of the fruit of the avocado tree *Persea americana*, the oil having lubricating, regenerative, and moisturizing properties.

Extract of Brahmi, also known by the INCI name *bacopa monniera* oil, is a non-aqueous extract derived from the leaves and flowers of the Brahmi plant, *Bacopa monniera*, a semi-aquatic herb. It is used to promote circulation in the scalp and promote hair growth. The extraction oil is preferably sesame oil, but other oils such as coconut oil are possible.

Emu oil is an oil made from the fat of the emu, *Dromaius novaehollandiae*. The largest component is oleic acid followed by linoleic acid with a small amount of linolenic acid. Emu oil replenishes lost oils and fats in the skin because the oil penetrates deeply without clogging pores.

Nettle extract, also known by its INCI name, *urtica dioica* extract, is an aqueous extract from the leaves of the stinging nettle *Urtica dioica*, a flowering herb, which is rich in trace minerals and Vitamins A and C, and has anti-inflammatory properties. It is a scalp treatment, particularly for dry scalp, promotes hair growth and gives hair gloss.

Rosemary extract, also known by its INCI name, *rosmarinus officinalis* leaf extract, is an essential oil, a non-aqueous extract from the leaves of the herbal rosemary plant also known as *Rosmarinus Officinalis*. It nourishes the scalp and stimulates hair follicles to encourage hair growth.

Sage extract, also known by its INCI name, *salvia officinalis* oil, is an essential oil obtained by steam distillation of the leaves of the sage shrub *Salvia Officinalis*, are used as a fragrant component in lotions. A non-aqueous extract, the essential oil has antioxidant and antibiotic properties. The oil contains thujone, which has many beneficial properties including being an antimicrobial.

Tea tree oil, also know by its INCI name, *melaleuca alternifolia* leaf oil, is an essential oil obtained by steam distillation of the leaves of *Melaleuca alternifolia*, and several other species in the malaleuca family. It is rich in terpenes, particularly terpinen-4-ol, as well as terpinenes. Tea tree oil is a non-aqueous extract, having antimicrobial and anti-fungal properties that promote a healthy scalp.

Sweet almond oil, also known by its INCI name, *prunus amygdalus dulcis* oil, is an oil obtained from dried kernels of sweet almonds and is primarily glyceryl oleate, with smaller amounts of polyunsaturated fatty acids. The oil is an emollient that softens and soothes the scalp and hair as well as acting as a skin lubricant.

The carrier systems in the embodiments of the post-shampoo treatment are oils that do not dissolve aqueous solutions and are generally not miscibly stable with aqueous solutions. The post-shampoo treatment must be vigorously shaken immediately before application to temporarily mix the nettle extract with the other oils to form a temporary emulsion.

Vitamin E is a naturally occurring vitamin with strong antioxidant properties. Vitamin E comes in a variety of homologs of tocopherols, such as tocopheryl acetate, tocotrienols. All forms of vitamin E are oil-soluble and can be used in the post-shampoo treatment. vitamin E prevents oxidative damage to scalp tissue as well as to any naturally occurring oils present in the scalp, preserving the post-shampoo treatment.

VATIKA® Brand Enriched Coconut Hair Oil is a product containing neem, extracts of Brahmi, amla, bahera and harar fruits, henna, lemon oil, rosemary oil, kapur kachri, milk extracts and coconut oil.

Example 4

The composition of an embodiment of the post-shampoo treatment is disclosed in Table 4.

TABLE 4

| Ingredient | Minimum | Maximum |
| --- | --- | --- |
| Jojoba oil | 30.5% | 49.0% |
| Grape seed oil | 30.5% | 49.0% |
| Vitamin E | 1.0% | 10.0% |
| Avocado oil | 1.0% | 10.0% |
| VATIKA Brand Enriched Coconut Hair Oil | Trace | 1.0% |
| Emu oil | Trace | 1.0% |
| Lavender oil | Trace | 1.0% |
| Rosemary oil extract | Trace | 1.0% |
| Sage oil extract | Trace | 1.0% |
| Nettle extract | Trace | 1.0% |
| Tea tree oil extract | Trace | 0.50% |
| Orange oil | 0% | 1.0% |
| Ylang ylang oil | 0% | 1.0% |
| Lemongrass oil | 0% | 0.50% |

The jojoba oil and grape seed oil compose the carrier system. Each may vary from the minimum of 30.5% to a maximum of 49.0% and are generally present in equal amounts. The vitamin E and avocado oil may vary from the minimum of 1% to a maximum of 10%, but are in a ratio of about 1:1 to each other. The other ingredients are generally present in small amounts and all the essential oils and extracts need not be present. For example, lavender oil may be present with or without one or more of the essential oils selected from the group consisting of orange oil, ylang ylang oil and lemongrass oil. Lavender oil is the preferred essential oil because of its therapeutic calming effect.

Example 5

The composition of one embodiment of the post-shampoo treatment is disclosed in Table 5.

TABLE 5

| Ingredient | Minimum | Maximum | Preferred |
| --- | --- | --- | --- |
| Jojoba oil | 30.5% | 49.0% | 42.0% |
| Grape seed oil | 30.5% | 49.0% | 42.0% |
| Vitamin E | 1.0% | 10.0% | 2.0% |
| Avocado oil | 1.0% | 10.0% | 2.0% |
| Coconut Oil | Trace | 1.0% | 1.0% |
| Emu oil | Trace | 1.0% | 1.0% |
| Lavender oil | Trace | 1.0% | 1.0% |
| Rosemary oil extract | Trace | 1.0% | 1.0% |
| Sage oil extract | Trace | 1.0% | 1.0% |
| Nettle extract | Trace | 1.0% | 1.0% |
| Tea tree oil extract | Trace | 1.0% | 1.0% |
| Extract of Brahmi in sesame oil | Trace | 2.5% | 2.5% |
| Amla extract in sesame oil | Trace | 2.5% | 2.5% |

The jojoba oil and grape seed oil compose the carrier system, as in Example 4. Each may vary from the minimum of 30.5% to a maximum of 49.0% and are generally present in equal amounts. The vitamin E and avocado oil may vary from the minimum of 1% to a maximum of 10%, but are in a ratio of about 1:1 to each other. The other ingredients are generally present in small amounts and the VATIKA Brand Enriched Coconut Hair Oil has been replaced with coconut oil along with small amounts of two extracts also present in VATIKA, namely, extract of Brahmi and amla extract.

Example 6

The composition of another embodiment of the post-shampoo treatment is disclosed in Table 6.

TABLE 6

| Ingredient | Minimum | Maximum |
| --- | --- | --- |
| Avocado oil | 27.0% | 40.0% |
| Sweet almond oil | 27.0% | 40.0% |
| Coconut oil | 5.0% | 20.0% |
| Vitamin E | 1.0% | 5.0% |
| Argan oil | 0.1% | 2.0% |
| Emu oil | 0.1% | 2.0% |
| Lavender oil | Trace | 1.0% |
| Rosemary oil extract | Trace | 1.0% |
| Sage oil extract | Trace | 1.0% |
| Nettle extract | Trace | 1.0% |
| Tea tree oil extract | Trace | 0.50% |
| Extract of Brahmi in sesame oil | Trace | 0.50% |
| Amla extract in sesame oil | Trace | 0.50% |

The carrier system is primarily avocado oil in combination with sweet almond oil at generally equal amounts. Each may vary from the minimum of 27.0% to a maximum of 40.0%. The coconut oil is also part of the carrier system and may vary from the minimum of 5.0% to a maximum of 20%. The primary components of the carrier are in a ratio of about 2:1 to 5:1 to the secondary component. Vitamin E and emu oil are also present with about twice as much vitamin E to emu oil. The other ingredients are generally present in small amounts. The lavender oil, sage oil, rosemary oil and tea tree oil are premixed with a small amount of sweet almond oil before addition to the post-shampoo treatment to aid in mixing. The aqueous nettle extract is also vigorously mixed with sweet almond oil before addition to the post-shampoo treatment.

It is understood that the above are examples of the composition of the post-shampoo treatment and that other oils in the carrier, other oils that contain antioxidants, antimicrobials, anti-inflammatory compounds, penetrating agents and other essential fragrance oils may be used while adhering to the inventive concept. It is also understood that the ratios of the ingredients disclosed hereinabove may be adjusted within the presented ranges. Such variations are contemplated as being a part of the present invention.

To use the rejuvenating hair oil system, the user applies a small amount of the pre-shampoo treatment to the hair and scalp and massages the treatment evenly into the hair into the scalp and distributes it through the hair. The user covers the hair and scalp with a plastic cap or a piece of plastic wrap, making sure the scalp and hair are completely covered. The user then waits about five to twenty minutes, and gently shampoos the pre-shampoo treatment off of the hair and scalp. The user can leave the treatment on the hair up to one hour if so desired or overnight before shampooing, depending on the condition of the hair, for example, if the hair is extremely dry, stressed, chemically treated and damaged. The pre-shampoo oil treatment acts as a barrier to protect the hair during the shampooing process from the harsh surfactants that are found in most shampoos. The user shampoos the hair gently dries the hair following his or her usual procedure.

After the user dries the hair, the post-shampoo treatment is applied to the scalp. The user vigorously shakes the post-shampoo treatment to mix the aqueous extracts into the oil and puts a plurality of drops, preferably three to four drops, directly onto the scalp. The user massages the post-shampoo treatment into the scalp and the roots of the hair near the scalp. The user may repeat application of the post-shampoo treatment as needed between shampooing, preferably three times a week for best results. The user preferably applies the post-shampoo treatment to the hair after it is dried, but the user may also apply the post-shampoo treatment to hair that is slightly damp. Within two weeks, the appearance of the hair improves, appearing more healthful.

The user repeats the pre-shampoo treatment, followed by shampooing, preferably on a weekly basis. The user repeats the post-shampoo treatment several times a week, preferably three times a week. Within approximately one year, the appearance of the hair improves, appearing more healthful, the length and the amount of the hair having increased.

Example 7

FIG. 1 is a photograph of a user taken at the beginning of treatment with the invention. Note that the hair does not lay flat, but clumps showing gaps where the hair is thinner.

Figure 2:
FIG. 2 is a photograph of the same user taken after one year of treatment with the invention.

FIG. 2 is a photograph of the same user taken after one year of treatment with the invention, showing longer, fuller, more healthful hair. In addition to the healthy appearance, the hair has lengthened more than the average 4.75 inches of annual growth. The hair lies flat without clumping, showing that all areas of the scalp have same high density of hair growth without gaps.

In conclusion, herein is presented a rejuvenating hair oil system with a pre-shampoo treatment and a post-shampoo treatment and a method of using the rejuvenating hair oil system that promotes healthful hair growth and improved hair appearance. The invention is illustrated by example in the tables, and throughout the written description. It should be understood that numerous variations are possible, while adhering to the inventive concept. Such variations are contemplated as being a part of the present invention.

What is claimed is:

1. A post-shampoo treatment composition that promotes healthful hair growth and improved hair appearance, comprising: jojoba oil in a range of thirty-nine and one-half percent to forty-nine percent, grape seed oil in a range of thirty-nine and one-half percent to forty-nine percent, vitamin E in a range of one percent to ten percent, avocado oil in a range of one percent to ten percent, coconut oil in a range of one percent to ten percent, emu oil in a range of one percent to ten percent, lavender oil in a range of a trace amount to one percent, rosemary oil extract in a range of a trace amount to one percent, sage oil extract in a range of a trace amount to one percent, nettle extract in a range of a trace amount to one percent, tea tree oil extract in a range of a trace amount to one-half percent, extract of Brahmi in sesame oil, and amla extract in sesame oil.

2. A post-shampoo treatment composition that promotes healthful hair growth and improved hair appearance, comprising: jojoba oil in a range of thirty-nine and one-half percent to forty-nine percent, grape seed oil in a range of thirty-nine and one-half percent to forty-nine percent, vitamin E in a range of one percent to ten percent, avocado oil in a range of one percent to ten percent, emu oil in a range of a trace amount to one percent, lavender oil in a range of a trace amount to one percent, rosemary oil extract in a range of a trace amount to one percent, sage oil extract in a range of a trace amount to one percent, nettle extract in a range of a trace amount to one percent, tea tree oil extract in a range of a trace amount to one-half percent, orange oil in a range of a trace amount to one percent, ylang ylang oil in a range of a trace amount to one percent, and lemongrass oil in a range of a trace amount to one-half percent.

3. A post-shampoo treatment composition that promotes healthful hair growth and improved hair appearance, comprising: avocado oil in a range of twenty-seven percent to forty percent, sweet almond oil in a range of twenty-seven percent to forty percent, coconut oil in a range of five percent to twenty percent, vitamin E in a range of one to five percent, argan oil in a range of one-tenth percent to two percent, emu oil in a range of one-tenth percent to two percent, lavender oil in a range of of a trace amount to one percent, rosemary oil extract in a range of of a trace amount to one percent, sage oil extract in a range of a trace amount to one percent, nettle extract in a range of a trace amount to one percent, tea tree oil extract in a range of a trace amount to one-half percent, extract of Brahmi in sesame oil, and amla extract in sesame oil.

* * * * *